United States Patent
Suh

(10) Patent No.: US 11,540,957 B2
(45) Date of Patent: Jan. 3, 2023

(54) ABSORBENT ARTICLE WITH PIVOTABLE WINGS

(71) Applicant: Kimberly-Clark Worldwide, Inc., Neenah, WI (US)

(72) Inventor: JaeAh Suh, Seoul (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 658 days.

(21) Appl. No.: 16/611,322

(22) PCT Filed: Mar. 28, 2018

(86) PCT No.: PCT/US2018/024782
§ 371 (c)(1),
(2) Date: Nov. 6, 2019

(87) PCT Pub. No.: WO2018/217295
PCT Pub. Date: Nov. 29, 2018

(65) Prior Publication Data
US 2020/0188196 A1    Jun. 18, 2020

Related U.S. Application Data

(60) Provisional application No. 62/511,487, filed on May 26, 2017.

(51) Int. Cl.
*A61F 13/56*    (2006.01)
*A61F 13/47*    (2006.01)
(Continued)

(52) U.S. Cl.
CPC ........ *A61F 13/5616* (2013.01); *A61F 13/472* (2013.01); *A61F 13/4704* (2013.01);
(Continued)

(58) Field of Classification Search
CPC .............. A61F 13/5616; A61F 13/4704; A61F 13/472; A61F 2013/4708; A61F 13/475;
(Continued)

(56) References Cited

U.S. PATENT DOCUMENTS 4,589,876 A    5/1986   Van Tilburg
4,940,462 A    7/1990   Salerno
(Continued)

FOREIGN PATENT DOCUMENTS

EP    1208823 A1    5/2002
JP    2003325578 A    11/2003
(Continued)

OTHER PUBLICATIONS

Always Maxi, https://www.amazon.com/Always-Infinity-Normal-Sanitary-Towels/dp/B01KA1FYV8/.

*Primary Examiner* — Michele M Kidwell
(74) *Attorney, Agent, or Firm* — Kimberly-Clark Worldwide, Inc.

(57) ABSTRACT

An absorbent article can have a pair of pivotable wings. The pair of pivotable wings can be formed from a wing material which can be bonded to a backsheet layer of the absorbent article and each wing can be configured to pivot between a first wing configuration and a second wing configuration. The wing material can be provided with a wing pivot point and fold lines which can enable the pivoting between the first wing configuration and the second wing configuration.

15 Claims, 9 Drawing Sheets

(51) Int. Cl.
   *A61F 13/472* (2006.01)
   *A61F 13/511* (2006.01)
   *A61F 13/514* (2006.01)
   *A61F 13/53* (2006.01)

(52) U.S. Cl.
   CPC ...... *A61F 13/511* (2013.01); *A61F 13/51474* (2013.01); *A61F 13/53* (2013.01); *A61F 2013/4708* (2013.01)

(58) Field of Classification Search
   CPC ................ A61F 13/476; A61F 13/5605; A61F 13/5611; A61F 2013/5688
   USPC .................................................... 604/385.04
   See application file for complete search history.

(56) References Cited

U.S. PATENT DOCUMENTS

| | | | |
|---|---|---|---|
| 5,125,918 A | 6/1992 | Seidy | |
| 5,154,715 A | 10/1992 | Van Iten | |
| 5,281,209 A | 1/1994 | Osborn et al. | |
| 5,344,416 A * | 9/1994 | Niihara | A61F 13/515 604/385.04 |
| 5,389,094 A | 2/1995 | Lavash et al. | |
| 5,558,657 A * | 9/1996 | Hammons | A61F 13/4753 604/385.04 |
| 5,578,026 A * | 11/1996 | Lavash | A61F 13/5616 604/389 |
| 5,643,245 A | 7/1997 | Osborn et al. | |
| 5,704,930 A * | 1/1998 | Lavash | A61F 13/515 604/385.24 |
| 5,772,648 A | 6/1998 | Osborn et al. | |
| 5,820,618 A | 10/1998 | Roberts et al. | |
| 6,030,373 A | 2/2000 | VanGompel et al. | |
| 6,171,291 B1 | 1/2001 | Osborn, III et al. | |
| 6,200,298 B1 | 3/2001 | Osborn, III et al. | |
| 6,280,428 B1 | 8/2001 | Lash et al. | |
| 6,328,722 B1 | 12/2001 | Lavash et al. | |
| 6,391,011 B1 | 5/2002 | Davis et al. | |
| 6,689,112 B1 * | 2/2004 | Blanchard | A61F 13/476 604/385.04 |
| 6,902,552 B2 | 6/2005 | VanGompel et al. | |
| 7,811,271 B2 * | 10/2010 | Digiacomantonio | A61F 13/5616 604/385.04 |
| 8,419,704 B2 | 4/2013 | Magnusson et al. | |
| 8,574,212 B2 | 11/2013 | Oku et al. | |
| 8,684,985 B2 * | 4/2014 | Odoi | A61F 13/15723 604/385.03 |
| 9,125,772 B2 * | 9/2015 | Eilers | A61F 13/472 |
| 9,198,810 B2 * | 12/2015 | Kuramochi | A61F 13/5616 |
| 11,234,871 B2 * | 2/2022 | Kuramochi | A61F 13/47236 |
| 11,357,672 B2 * | 6/2022 | Yonaha | A61F 13/15747 |
| 2012/0238986 A1 * | 9/2012 | Digiacomantonio | A61F 13/84 604/385.04 |
| 2014/0343525 A1 | 11/2014 | Roh et al. | |
| 2015/0018796 A1 * | 1/2015 | Tamura | A61F 13/4704 604/385.04 |
| 2021/0121335 A1 * | 4/2021 | Anousis | A61F 13/581 |

FOREIGN PATENT DOCUMENTS

| | | |
|---|---|---|
| KR | 20060017738 A | 2/2006 |
| KR | 20140075494 A | 6/2014 |
| WO | 9610977 A1 | 4/1996 |
| WO | 16032488 A1 | 3/2016 |
| WO | 16209914 A1 | 12/2016 |

* cited by examiner

ABSORBENT ARTICLE WITH PIVOTABLE WINGS

BACKGROUND OF THE DISCLOSURE

Products such as absorbent articles are often used to collect and retain human body exudates containing, for example, urine, menses, and/or blood. Comfort, absorbency, and discretion are three main product attributes and areas of concern for the wearer of the absorbent article. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, and pantiliners. These products generally have an absorbent core positioned between a body-facing liquid permeable topsheet layer and a garment-facing liquid impermeable backsheet layer. The edges of the topsheet layer and the backsheet layer are often bonded together at their periphery to form a seal to contain the absorbent core and body exudates received into the product through the topsheet layer. In use, products such as, for example, feminine pads and sanitary napkins are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or liquid impermeable layers.

One problem with such conventional absorbent articles is that the wing-like structures currently provided on absorbent articles may not provide the desired coverage for the wearer of the absorbent article. Many of the wing-like structures of current absorbent articles can be too small to provide adequate side leakage protection, such as, for protection of the wearer's undergarments. A prior attempt to correct this problem has included providing longer integral wing-like structures but as these structures have been integral with the absorbent article, they increase the tension on the absorbent article when attached to the wearer's undergarment and can result in pulling the absorbent article away from the wearer reducing the fit of the absorbent article to the wearer.

As a result, there remains a need for an improved product, such as an absorbent article with discreetly attached wings that can change size as desired by the wearer without negatively impacting the fit of the absorbent article to the wearer.

SUMMARY OF THE DISCLOSURE

In various embodiments, an absorbent article can have a first transverse direction end edge, a second transverse direction end edge, and a pair of longitudinal direction side edges extending between and connecting the first transverse direction end edge and the second transverse direction end edge; a topsheet layer, a backsheet layer, and an absorbent core positioned between the topsheet layer and the backsheet layer; a longitudinal direction centerline; a pair of wings bonded to the backsheet layer, each of the pair of wings comprising a wing material, each wing material comprising a wing pivot point; a first material internal edge which has a first proximal end and a first distal end and a second material internal edge which has a second proximal end and a second distal end, wherein the first proximal end and the second proximal end of the respective first material internal edge and the second material internal edge join together at the wing pivot point and each of the first material internal edge and the second material internal edge extend in a direction away from the wing pivot point and towards the longitudinal direction centerline; an exterior material edge extending between and connecting the first distal end and the second distal end of the respective first material internal edge and the second material internal edge and extending in a direction away from the longitudinal direction centerline such that at least a portion of the exterior material edge extends beyond one of the longitudinal direction side edges of the absorbent article; a first fold line having a third proximal end and a third distal end, a second fold line having a fourth proximal end and a fourth distal end, a third fold line having a fifth proximal end and a fifth distal end, and a fourth fold line having a sixth proximal end and a sixth distal end, wherein each of the third proximal end, the fourth proximal end, the fifth proximal end, and the sixth proximal end join together at the wing pivot point and each of the first fold line, second fold line, third fold line, and fourth fold line extend from the wing pivot point to the exterior material edge; and a first attachment region bordered by the first material internal edge, the first fold line, and a portion of the exterior material edge; a second attachment region bordered by the second material internal edge, the fourth fold line, and a portion of the exterior material edge; a first fold region bordered by the first fold line, the second fold line, and a portion of the exterior material edge; a second fold region bordered by the third fold line, the fourth fold line, and a portion of the exterior material edge, and a wing outer region bordered by the second fold line, the third fold line, and a portion of the exterior material edge.

In various embodiments, each of the first fold line and second fold lines are in an unfolded configuration such that at least a portion of the wing outer region and a portion of the first fold region extend beyond the longitudinal direction side edges of the absorbent article, and each of the third fold lines and fourth fold lines are in a folded configuration such that at least a portion of the wing outer region and the second fold region is positioned in an overlapping configuration with the backsheet layer.

In various embodiments, each of the first fold line and second fold lines are in a folded configuration such that the first fold region is positioned in an overlapping configuration with the backsheet layer, and each of the third fold lines and the fourth fold lines are in an unfolded configuration such that at least a portion of the wing outer region and the second fold region extend beyond the longitudinal direction side edges of the absorbent article.

In various embodiments, the first fold line and the fourth fold line are at a 180 degree angle to each other. In various embodiments, the second fold line and the third fold line are at a 180 degree angle to each other.

In various embodiments, the first fold line and the fourth fold line are parallel to the longitudinal direction side edge.

In various embodiments, the first fold line and the fourth fold line are in a fixed spatial relationship to the longitudinal direction centerline. In various embodiments, the second fold line and the third fold line can rotate their spatial relationship to the longitudinal direction centerline.

In various embodiments, the first fold line is at an angle to the second fold line of from about 5 degrees to about 85 degrees. In various embodiments, the third fold line is at an angle to the fourth fold line of from about 5 degrees to about 85 degrees. In various embodiments, an angle between the first fold line and the second fold line is the same as an angle between the third fold line and the fourth fold line.

In various embodiments, the wing pivot point is located proximal to one of the longitudinal direction side edges. In various embodiments, the wing pivot point is located at a distance, in a transverse direction of the absorbent article, away from one of the longitudinal direction side edges.

In various embodiments, the absorbent article further has a garment attachment. In various embodiments, the garment attachment does not interfere with the functionality of the wings.

Figure 1:
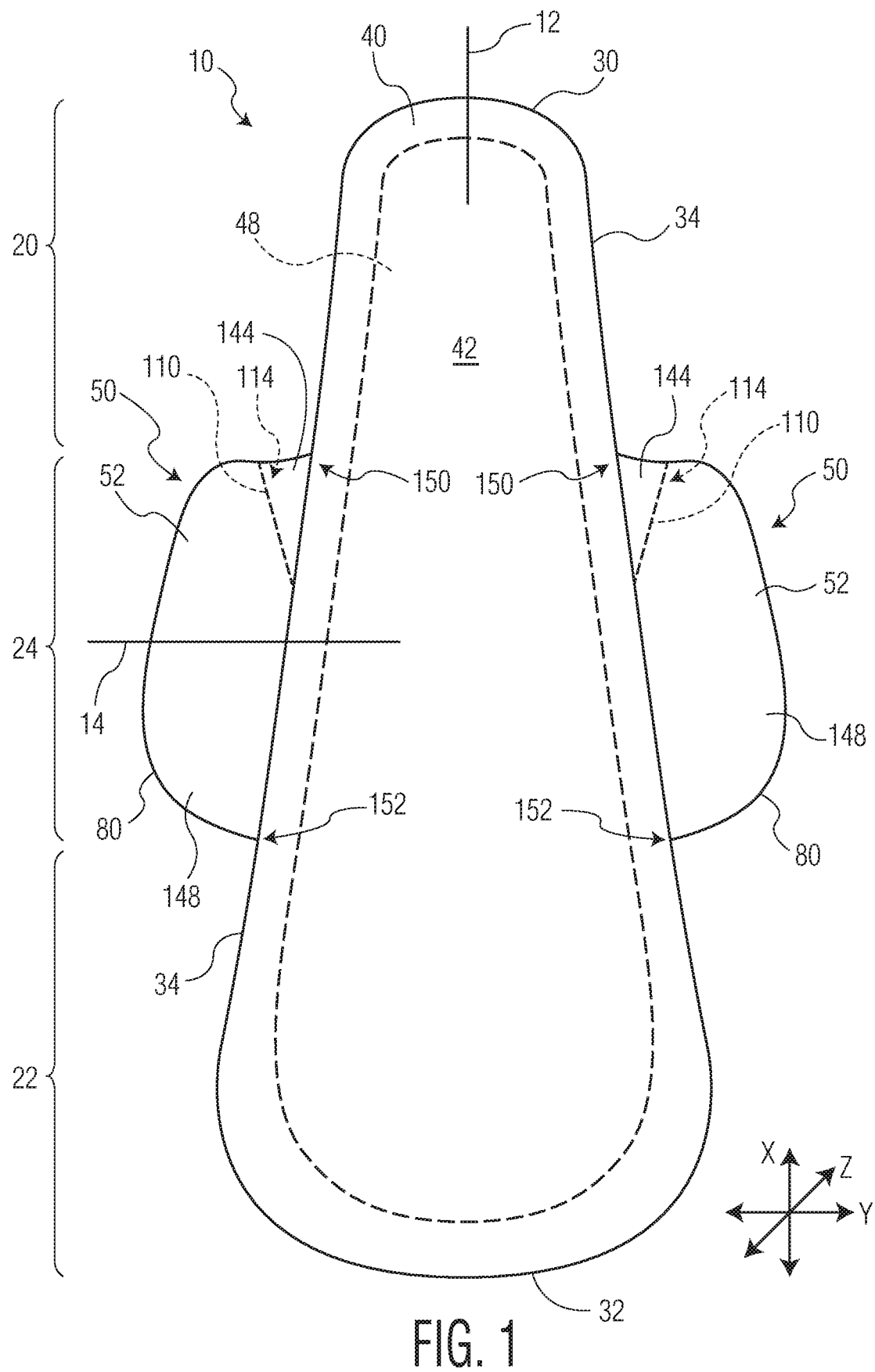
FIG. 1 is a top view of an embodiment of an absorbent article with the wings in a first configuration.

Repeat use of reference characters in the present specification and drawings is intended to represent the same or analogous features or elements of the disclosure.

DETAILED DESCRIPTION OF THE DISCLOSURE

The present disclosure is directed towards an absorbent article which can have a pair of pivotable wings. In use, absorbent article wings drape over the edges of the wearer's undergarment and can form a barrier along those undergarment edges to prevent body exudates from coming into contact with the wearer's undergarment. An absorbent article having pivotable wings can provide a wearer of the absorbent article with a choice as to the amount of area of wing that the wearer prefers to drape over the edges of their undergarment. The pair of pivotable wings can be formed from a wing material which can be bonded to a backsheet layer of the absorbent article and each wing can be configured to pivot between a first wing configuration and a second wing configuration. Each of the first wing configuration and the second wing configuration define a first area of the wing and a second area of the wing, respectively, of the wing material which extends outwardly beyond a longitudinal direction side edge of the absorbent article. The second area of the wing can be greater than the first area of the wing and can provide additional protection against and prevention of soiling of the wearer's undergarment.

Definitions

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, feminine hygiene products including, but not limited to, menstrual pads, sanitary napkins, feminine pads, pantiliners, and panty shields, and incontinence products, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Absorbent Article:

The present disclosure is directed towards an absorbent article which can have a pair of pivotable wings. In use, absorbent article wings drape over the edges of the wearer's undergarment and can form a barrier along those undergarment edges to prevent body exudates from coming into contact with the wearer's undergarment. An absorbent article having pivotable wings can provide a wearer of the absorbent article with a choice as to the amount of area of wing that the wearer prefers to drape over the edges of their undergarment. The pair of pivotable wings can be formed from a wing material which can be bonded to a backsheet layer of the absorbent article and each wing can be configured to pivot between a first wing configuration and a second wing configuration. Each of the first wing configuration and the second wing configuration define a first area of the wing and a second area of the wing, respectively, of the wing material which extends outwardly beyond a longitudinal direction side edge of the absorbent article. The second area of the wing can be greater than the first area of the wing and can provide additional protection against and prevention of soiling of the wearer's undergarment.

Referring to FIGS. 1-4, an absorbent article 10 of the present disclosure is exemplified in the form of a feminine hygiene product such as a menstrual pad or sanitary napkin. The absorbent article 10 can have a longitudinal direction (X), a transverse direction (Y), and a depth direction (Z). The absorbent article 10 can have a longitudinal centerline 12 and a transverse centerline 14. The absorbent article 10 can have an anterior region 20, a posterior region 22, and a central region 24 located between the anterior region 20 and the posterior region 22. The absorbent article 10 can have a first transverse direction end edge 30, a second transverse direction end edge 32 opposed to the first transverse direction end edge 30, and a pair of opposing longitudinal direction side edges 34 extending between and connecting the first and second transverse direction end edges, 30 and 32. The absorbent article 10 can have a wearer facing, liquid permeable topsheet layer 40 and a garment facing, liquid impermeable backsheet layer 44. An absorbent core 48 can be positioned between the topsheet layer 40 and the backsheet layer 44. The topsheet layer 40 and the backsheet layer 44 can both extend beyond the outermost peripheral edges of the absorbent core 48 and can be peripherally bonded together, either entirely or partially, using known bonding techniques to form a sealed peripheral region. For example, the topsheet layer 40 and the backsheet layer 44 can be bonded together by adhesive bonding, ultrasonic bonding, or any other suitable bonding technique known in the art.

Figure 2:
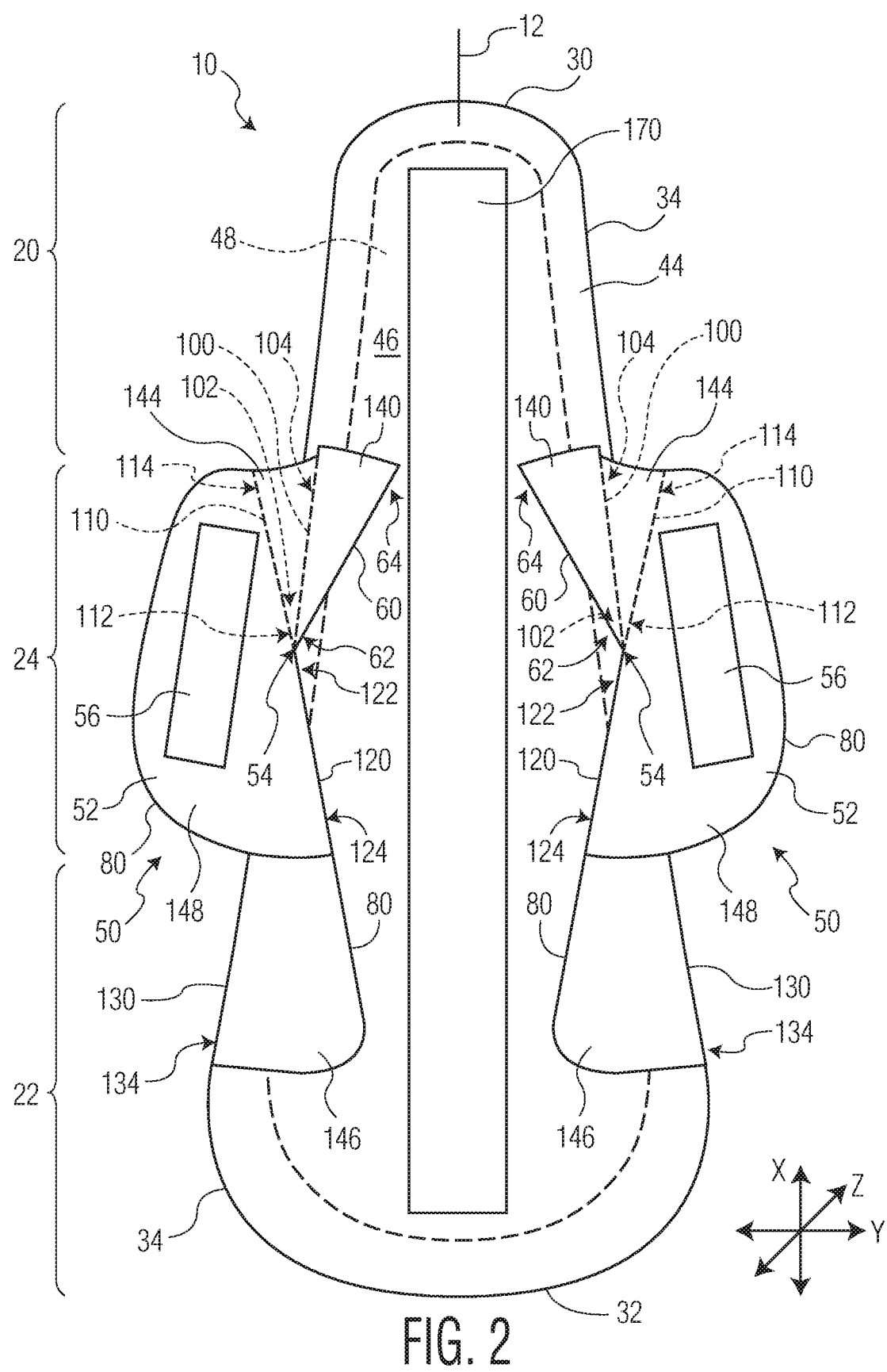
FIG. 2 is a bottom view of the absorbent article of FIG. 1.
Figure 3:
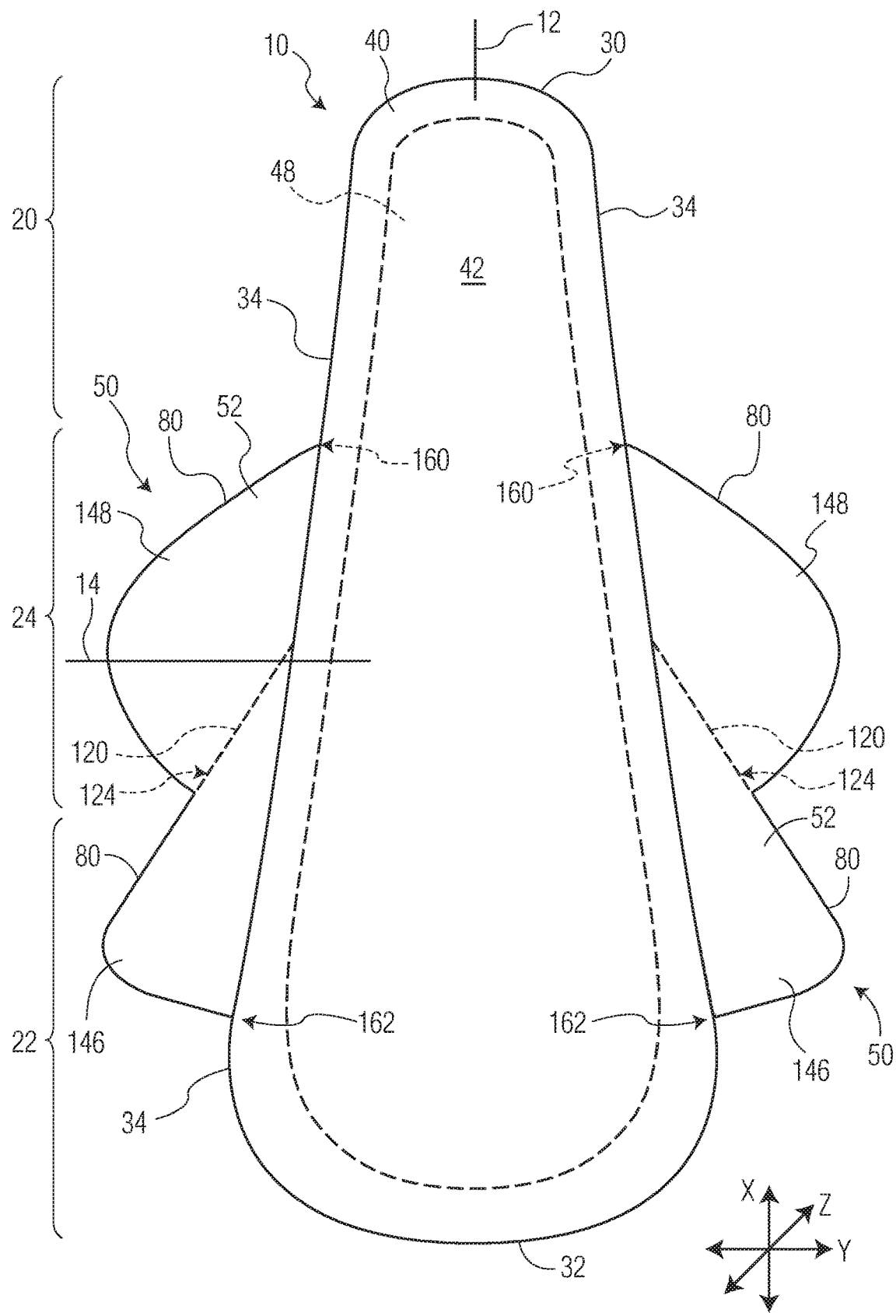
FIG. 3 is a top view of an embodiment of an absorbent article with the wings in a second wing configuration.
Figure 4:
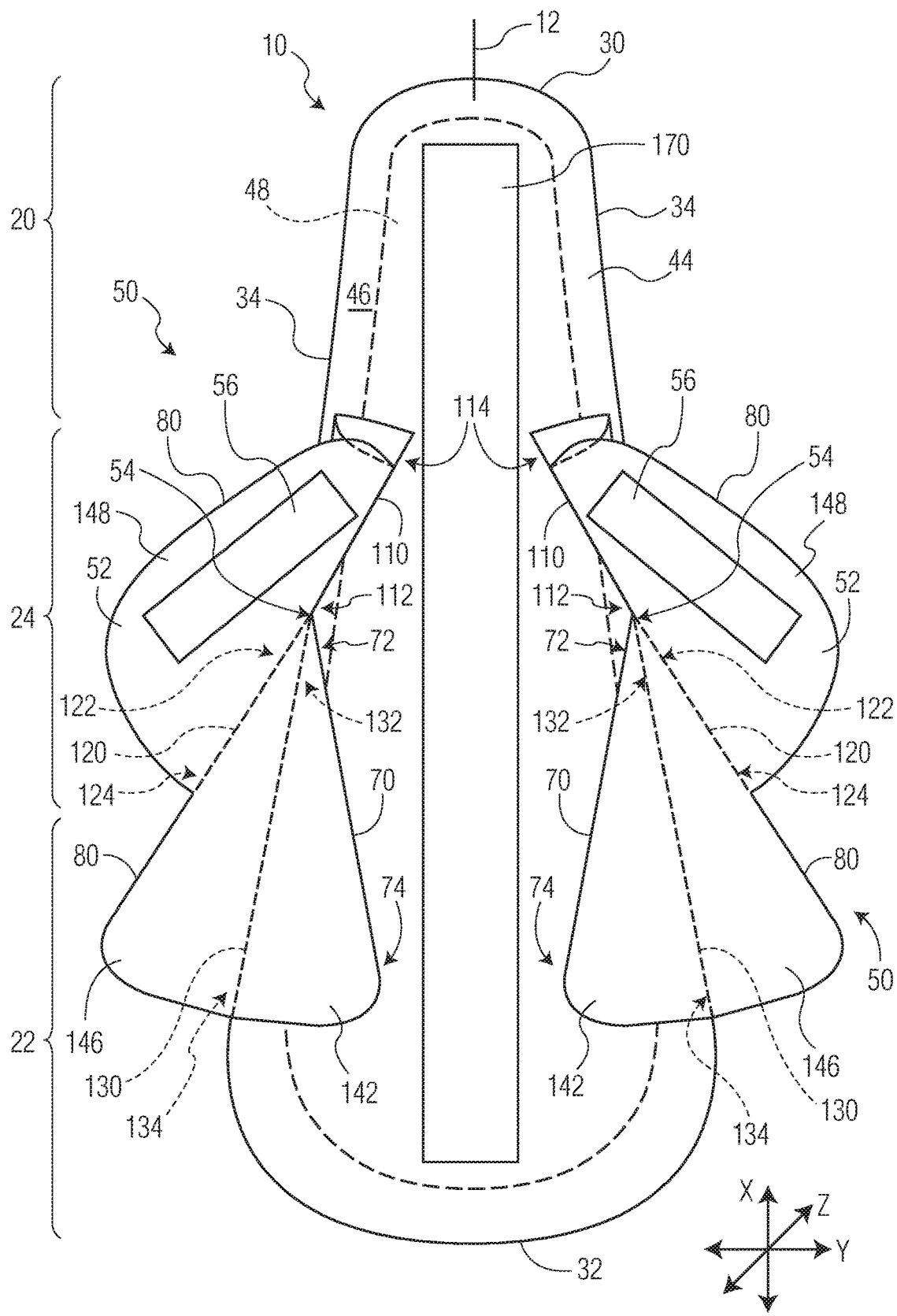
FIG. 4 is a bottom view of the absorbent article of FIG. 3.

The absorbent article 10 can further have a pair of wings 50 extending outwardly, in the transverse direction (Y), from the absorbent article 10. The wings 50 can drape over the edges of the wearer's undergarment so that the wings 50 are disposed between the edges of the wearer's undergarment and her thighs. The wings 50 can serve at least two purposes. First, the wings 50 can prevent soiling of the wearer's undergarment by forming a barrier along the edges of the undergarment. Second the wings 50 can be provided with an attachment aid 56, such as, for example, a garment attachment adhesive or a hook, to keep the absorbent article 10 securely and properly positioned in the undergarment. Each wing 50 can fold under the crotch region of the wearer's undergarment and the attachment aid 56 can either form a secure attachment to the opposite wing 50 or directly to the surface of the wearer's undergarment. Each of the wings 50 can be configured to pivot between a first wing configuration and a second wing configuration. An exemplary embodiment of a first wing configuration is illustrated in FIGS. 1 and 2 and an exemplary embodiment of a second wing configuration is illustrated in FIGS. 3 and 4. A pivotable wing 50 can enable the wearer of the absorbent article 10 to select the wing configuration of the pair of wings 50 which will be more suitable for their particular needs. Each of the wings 50 can be configured from a wing material 52 which has a wing pivot point 54 from which fold lines, 100, 110, 120, and 130, can emanate. The fold lines, 100, 110, 120, and 130, enable portions of the wing material 52 to unfold and portions of the wing material 52 to fold over onto itself as the wings 50 pivot from the first wing configuration to the second wing configuration.

Each of these components of the absorbent article 10, as well as additional components, will be described in more detail herein.

Topsheet Layer:

The topsheet layer 40 defines a body facing surface 42 of the absorbent article 10 that may directly contact the body of the wearer and is liquid permeable to receive body exudates. The topsheet layer 40 is desirably provided for comfort and functions to direct body exudates away from the body of the wearer, through its own structure, and towards the absorbent core 48. The topsheet layer 40 desirably retains little to no liquid in its structure, so that it provides a relatively comfortable and non-irritating surface next to the skin of the wearer of the absorbent article 10.

The topsheet layer 40 can be a single layer of material, or alternatively, can be multiple layers that have been laminated together. The topsheet layer 40 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 40.

In various embodiments the topsheet layer 40 can be constructed from various nonwoven webs such as meltblown webs, spunbond webs, hydroentangled spunlace webs, or through air bonded carded webs. Examples of suitable topsheet layer 40 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 40 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 40, each of which is hereby incorporated by reference thereto in its entirety. Additional topsheet layer 40 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 40 may contain a plurality of apertures formed therethrough to permit body exudates to pass more readily into the absorbent core 48. The apertures may be randomly or uniformly arranged throughout the topsheet layer 40. The size, shape, diameter, and number of apertures may be varied to suit an absorbent article's 10 particular needs.

In various embodiments, the tosphheet layer 40 can have a basis weight ranging from about 5, 10, 15, 20, or 25 gsm to about 50, 100, 120, 125, or 150 gsm. For example, in an embodiment, a topsheet layer 40 can be constructed from a through air bonded carded web having a basis weight ranging from about 15 gsm to about 100 gsm. In another example, a topsheet layer 40 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 40 can be at least partially hydrophilic. In various embodiments, a portion of the topsheet layer 40 can be hydrophilic and a portion of the topsheet layer 40 can be hydrophobic. In various embodiments, the portions of the topsheet layer 40 which can be hydrophobic can be either an inherently hydrophobic material or can be a material treated with a hydrophobic coating.

In various embodiments, the topsheet layer 40 can be a multicomponent topsheet layer 40 such as by having two or more different nonwoven or film materials, with the different materials placed in separate locations in the transverse direction (Y) of the absorbent article 10. For example, the topsheet layer 40 can be a two layer or multicomponent material having a central portion positioned along and straddling a longitudinal centerline 12 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 40 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 40 can be positioned symmetrically about the absorbent article 10 longitudinal centerline 12. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 40. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 40. The selection of such topsheet layer 40 materials can vary based upon the overall desired attributes of the topsheet layer 40. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 40 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 40. The film layer may also serve as a barrier layer to prevent rewet of the topsheet layer 40 as well as to prevent the flow of fluid off the side edges of the absorbent article 10. In various embodiments, the side portions can be laminates such as a spunbond-meltblown-meltblown-spunbond layer ("SMMS") laminate, spunbond-film laminate, or alternatively, other nonwoven laminate combinations.

Absorbent Core:

An absorbent core 48 can be positioned between the topsheet layer 40 and the backsheet layer 44 of the absorbent article 10. The absorbent core 48 can generally be any single layer structure or combination of layer components, which can demonstrate some level of compressibility, conformability, be non-irritating to the wearer's skin, and capable of absorbing and retaining liquids and other body exudates. In various embodiments, the absorbent core 48 can be formed from a variety of different materials and can contain any number of desired layers. For example, the absorbent core 48 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 48 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 48 in any amount as desired.

Regardless of the combination of absorbent materials used in the absorbent core 48, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 48 can vary as desired and can comprise any one of various shapes including, but not limited to, triangular, rectangular, dog-bone, elliptical, trapezoidal, T-shape, I-shape, and hourglass shapes. In various embodiments, the absorbent core 48 can have a shape that generally corresponds with the overall shape of the absorbent article 10. The dimensions of the absorbent core 48 can be substantially similar to those of the absorbent article 10, however, it will be appreciated that the dimensions of the absorbent core 48 while similar, will often be less than those of the overall absorbent article 10, in order to be adequately contained therein.

By way of example, suitable materials and/or structures for the absorbent core 48 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 48 can be a single layer structure and can include, for example, a matrix of cellulosic fluff and superabsorbent material. In various embodiments, an absorbent core 48 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 48 may be constructed of an airlaid material and the garment facing layer of the absorbent core 48 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 44 is generally liquid impermeable and is the portion of the absorbent article 10 which faces the garments of the wearer. The backsheet layer 44 can permit the passage of air or vapor out of the absorbent article 10 while still blocking the passage of liquids. Any liquid impermeable material may generally be utilized to form the backsheet layer 44. The liquid impermeable layer 44 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 44 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 44 can be a polyethylene film such as that obtainable from Pliant Corp., Schaumburg, Ill., USA. Another example can include calcium carbonate-filled polypropylene film. In still another embodiment, the backsheet layer 44 can be a hydrophobic nonwoven material with water barrier properties such as a nonwoven laminate, an example of which can be a spunbond, meltblown, meltblown, spunbons, four-layered laminate.

In various embodiments, the backsheet layer 44 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent article 10 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, Ind., U.S.A.

The backsheet layer 44 can, therefore, be of a single or multiple layer construction, such as of multiple film layers or laminates of film and nonwoven fibrous layers. Suitable backsheet layers 44 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Wings:

Referring to the Figures, in various embodiments, the absorbent article 10 can have a pair of pivotable wings 50 extending outwardly, in the transverse direction (Y), from the absorbent article 10. In use, the wings 50 can drape over the edges of the wearer's undergarment so that the wings 50 are disposed between the edges of the wearer's undergarment and her thighs. The wings 50 can serve at least two purposes. First, the wings 50 can prevent soiling of the wearer's undergarment by forming a barrier along the edges of the undergarment. Second, the wings 50 can be provided with an attachment aid 56, such as, for example, a garment attachment adhesive or a hook, to keep the absorbent article 10 securely and properly positioned in the undergarment. The wings 50 can wrap around the crotch region of the wearer's undergarment to aid in securing the absorbent article 10 to the wearer's undergarment when in use. Each wing 50 can fold under the crotch region of the wearer's undergarment and the attachment aid 56 can either form a secure attachment to the opposite wing 50 or directly to the surface of the wearer's undergarment.

In various embodiments, the wings 50 can be constructed of a wing material 52 which can be a material the same as or similar to the topsheet layer 40, the backsheet layer 44, or combinations of these materials. The wing material 52 forming each wing 50 can be a separate element of the absorbent article 10 and can be bonded to the main body of the absorbent article 10, such as, for example, by being bonded to the backsheet layer 44. In various embodiments, the wing material 52 forming the wings 50 can be bonded to the garment facing surface 46 of the backsheet layer 44. In various embodiments, the wing material 52 forming the wings 50 can be bonded to the body facing surface of the backsheet layer 44.

Each wing 50 can be configured to pivot between a first wing configuration and a second wing configuration. An example of a first wing configuration is illustrated in FIGS. 1 and 2 and an example of a second wing configuration is illustrated in FIGS. 3 and 4. A pivotable wing 50 can enable the wearer of the absorbent article 10 to select the wing configuration of the pair of wings 50 which will be more suitable for their particular needs. In order for the wings 50 to pivot between the first wing configuration and the second wing configuration, the wing material 52 forming each wing 50 is provided with a wing pivot point 54. Portions of the wing material 52 can rotate about the wing pivot point 54 during the transition between the first wing configuration and the second wing configuration.

When bonded to the absorbent article 10 the wing material 52 can have a longitudinal length which can be defined as the distance between a point of the wing material 52 located closest to the first transverse direction end edge 30 of the absorbent article 10 and a point of the wing material 52 located closest to the second transverse direction end edge 32 of the absorbent article 10. In various embodiments, when bonded to the absorbent article 10, the wing material 52 can have a wing pivot point 54 positioned at the midpoint of the longitudinal length of the wing material 52. In various embodiments, when bonded to the absorbent article 10, the wing material 52 can have a wing pivot point 54 positioned between the midpoint of the longitudinal length of the wing material 52 and the point of the wing material 52 closest to the first transverse direction end edge 30 of the absorbent article 10. In various embodiments, when bonded to the absorbent article 10, the wing material 52 can have a wing pivot point 54 positioned between the midpoint of the longitudinal length of the wing material 52 and the point of the wing material 52 closest to the second transverse direction end edge 32 of the absorbent article 10. In the exemplary embodiment illustrated in FIGS. 1-4, the wing pivot point 54 of the wing material 52 is positioned between the midpoint of the longitudinal length of the wing material 52 and the point of the wing material 52 closest to the first transverse direction end edge 30 of the absorbent article 10. In various embodiments, when bonded to the absorbent article 10 the wing pivot point 54 of the wing material 52 can be positioned in proximity to a longitudinal direction side edge 34 of the absorbent article 10. In various embodiments, when bonded to the absorbent article 10 the wing pivot point 54 of the wing material 52 can be positioned at a distance, in the transverse direction (Y), from a longitudinal direction side edge 34 of the absorbent article 10. In such embodiments in which the wing pivot point 54 is positioned at a distance away from a longitudinal direction side edge 34, when the wearer of the absorbent article 10 configures the wings 50 to wrap about her underwear the wings 50 may not cause tension within the absorbent article 10 which may result in the longitudinal direction side edges 34 also not being pulled down around the wearer's underwear, thus, maintaining a better fit of the absorbent article 10 to the body of the wearer.

The wing material 52 can have a shape which can be defined by a perimeter. The perimeter can include material internal edges, 60 and 70, and an exterior material edge 80. When the wing material 52 is bonded to the absorbent article 10 each of the material internal edges, 60 and 70, of the wing material 52 are positioned between the longitudinal direction side edges 34 of the absorbent article 10 and the longitudinal centerline 12 of the absorbent article 10. When the wing material 52 is bonded to the absorbent article 10 at least a portion of the exterior material edge 80 extends in a direction transversely outward beyond the longitudinal direction side edges 34 and at least a portion of the exterior material edge 80 is positioned between the longitudinal direction side edges 34 of the absorbent article 10 and the longitudinal centerline 12 of the absorbent article 10. Each of the material internal edges, 60 and 70, can have a proximal end, 62 and 72, respectively, and a distal end, 64 and 74, respectively. Each of the proximal ends, 62 and 72, respectively, can join together at the wing pivot point 54. From the wing pivot point 54, the material internal edges, 60 and 70, can emanate away from the wing pivot point 54 and in a direction towards the longitudinal centerline 12 such that the distal ends, 64 and 74, of each of the material internal edges, 60 and 70, respectively, are closer to the longitudinal centerline 12 than the proximal ends, 62 and 72, of the material internal edges, 60 and 70, respectively. The exterior material edge 80 can extend between and connect the distal ends, 64 and 74, of the material internal edges, 60 and 70, respectively. The exterior material edge 80 can extend in a direction away from the longitudinal centerline 12 such that at least a portion of the exterior material edge 80 extends beyond the longitudinal direction side edges 34 of the absorbent article 10. The material internal edges, 60 and 70, and the exterior material edge 80 together define the perimeter of the wing material 52.

As illustrated in FIGS. 1 and 2, when the wings 50 are in a first wing configuration portions of the wing material 52 are in a folded configuration and portions of the wing material 52 are in an unfolded configuration. As illustrated in FIGS. 3 and 4, when the wings 50 are in a second wing configuration those portions of the wing material 52 which were in an unfolded configuration in the first wing configuration are now folded and those portions which were folded in the first wing configuration are now unfolded in the second wing configuration. In order to effect the folding and unfolding of the portions of the wings 50, the wing material 52 can have fold lines, such as, for example, fold lines 100, 110, 120, and 130. These fold lines, 100, 110, 120, and 130, can join together at the wing pivot point 54 and emanate away from the wing pivot point 54 and towards the exterior material edge 80 of the wing material 52. Each of the fold lines, 100, 110, 120, and 130, can have a proximal end, 102, 112, 122, and 132, respectively, and a distal end, 104, 114, 124, and 134, respectively. Each of the proximal ends, 102, 112, 122, and 132, can join together at the wing pivot point 54. From the wing pivot point 54, each of the fold lines, 100, 110, 120, and 130, can emanate away from the wing pivot point 54 towards the exterior material edge 80 and the distal ends, 104, 114, 124, and 134, of each of the fold lines, 100, 110, 120, and 130, respectively, can contact the exterior material edge 80. The fold lines, 100, 110, 120, and 130, enable portions of the wing material 52 to unfold and portions of the wing material 52 to fold over onto itself as the wings 50 pivot from the first wing configuration to the second wing configuration.

Each of the fold lines, 100, 110, 120, and 130, can be configured into the wing material 52 at an angle to each other fold line, 100, 110, 120, and 130. In various embodiments, when the wing material 52 is bonded to the absorbent article 10, the first fold line 100 can emanate away from the wing pivot point 54 in a direction that is exactly opposite from the direction of the fourth fold line 130, thus, the first fold line 100 can be at an angle of 180 degrees from the fourth fold line 130 when the wing material 52 is bonded to the absorbent article 10. Similarly, in various embodiments, when the wing material 52 is bonded to the absorbent article 10, the second fold line 110 can emanate away from the wing pivot point 54 in a direction that is exactly opposite from the direction of the third fold line 120, thus, the second fold line 110 can be at an angle of 180 degrees from the third fold line 120 when the wing material 52 is bonded to the absorbent article 10. In various embodiments, the angle between the first fold line 100 and the second fold line 110 can be from about 5, 10, 15, 20, 25, 30, 35, 40, or 45 degrees to about 50, 55, 60, 65, 70, 75, 80, or 85 degrees. In various embodiments, the angle between the first fold line 100 and the second fold line 110 can be from about 20 or 25 degrees to about 30 or 35 degrees. In various embodiments, the angle between the third fold line 120 and the fourth fold line 130 can be from about 5, 10, 15, 20, 25, 30, 35, 40, or 45 degrees to about 50, 55, 60, 65, 70, 75, 80, or 85 degrees. In various embodiments, the angle between the third fold line 120 and the fourth fold line 130 is from about 20 or 25 degrees to about 30 or 35 degrees. In various embodiments, the angle between the first fold line 100 and the second fold line 110 can be the same as the angle between the third fold line 120 and the fourth fold line 130.

Each of the fold lines, 100, 110, 120, and 130, and the material internal edges, 60 and 70, can segment the wing material 52 into different wing regions. A first attachment region 140 can be bordered by the material internal edge 60, the first fold line 100, and a portion of the exterior material edge 80. A second attachment region 142 can be bordered by the material internal edge 70, the fourth fold line 130, and a portion of the exterior material edge 80. A first fold region 144 can be bordered by the first fold line 100, the second fold line 110, and a portion of the exterior material edge 80. A second fold region 146 can be bordered by the third fold line 120, the fourth fold line 130, and a portion of the exterior material edge 80. A wing outer region 148 can be bordered by the second fold line 110, the third fold line 120, and a portion of the exterior material edge 80.

The first attachment region 140 and the second attachment region 142 bond the wing material 52 to the backsheet layer 44 of the absorbent article 10. The first attachment region 140 and the second attachment region 142 can each be any size and shape deemed suitable to maintain bonding of the wing material 52 to the absorbent article 10. In various embodiments, the first attachment region 140 and the second attachment region 142 can have a length in the longitudinal direction (X) that is shorter than the length of the first fold line 100 and fourth fold line 130, respectively. In various embodiments, the first attachment region 140 and the second attachment region 142 can have a length in the longitudinal direction (X) that is at least as long as the first fold line 100 and the fourth fold line 130, respectively. In various embodiments, the first attachment region 140 and the second attachment region 142 can have a length in the longitudinal direction (X) that can be longer than the length of each of the first fold line 100 and the fourth fold line 130, respectively. Each of the first attachment region 140 and the second attachment region 142 can have an angle between their respective bordering material internal edges, 60 and 70, respectively, and their respective bordering fold lines, 100 and 130, respectively. In various embodiments, the angle between the material internal edge 60 and the first fold line 100 can be from about 10, 20, 30, or 45 degrees to about 50, 60, 75, 80, or 90 degrees. In various embodiments, the angle between the material internal edge 70 and the fourth fold line 130 can be from about 10, 20, 30, or 45 degrees to about 50, 60, 75, 80 or 90 degrees. In various embodiments, the angle between the material internal edge 60 and the first fold line 100 of the first attachment region 140 can be the same as the angle between the material internal edge 70 and the fourth folding line 130 of the second attachment region 142. In various embodiments, the angle between the material internal edge 60 and the first fold line 100 of the first attachment region 140 can be different from the angle between the material internal edge 70 and the fourth fold line 130 of the second attachment region 142. In various embodiments, an angle can also be present between the material internal edges, 60 and 70, which can be from about 0, 15, 30, 45 or 70 degrees to about 90, 115, 145, 160, or 180 degrees when the wing material 52 is not bonded to the absorbent article 10. In various embodiments, the angle between the material internal edges, 60 and 70, can be from about 45 or 70 degrees to about 90 or 145 degrees when the wing material 52 is bonded to the absorbent article 10.

Referring to FIGS. 1 and 2, the absorbent article 10 can have a pair of pivotable wings 50 present in a first wing configuration. In such a first wing configuration, each of the first attachment region 140 and the second attachment region 142 are bonded to the backsheet layer 44 of the absorbent article 10. The fourth fold line 130 is in a folded configuration such that the second fold region 146 is in an overlapping configuration with the second attachment region 142. The third fold line 120 is also folded such that a portion of the wing outer region 148 is in an overlapping configuration with the second fold region 146. Thus, in first wing configuration, the second fold region 146 and the portion of the wing outer region 148 which is in an overlapping configuration with the second fold region 146 is not visible to a wearer when the wearer views the absorbent article 10 in a top down view observing the absorbent article 10 with the topsheet layer 40 facing the wearer. In the first wing configuration, the first fold line 100 and the second fold line 110 are each in an unfolded configuration. Thus, in the first wing configuration, the first fold region 144 as well as a portion of the wing outer region 148 is visible to the wearer of the absorbent article 10 when the wearer views the absorbent article 10 in a top down view observing the absorbent article 10 with the topsheet layer 40 facing the wearer.

In the first wing configuration, the wing 50 that is visible to the wearer of the absorbent article 10 when observing the absorbent article 10 in a top down view with the topsheet layer 40 facing the wearer can have a first wing length. The first wing length can be defined as the distance between the first crossover point 150 and the second crossover point 152. Each of the first crossover points, 150 and 152, are those locations where the exterior material edge 80 of the wing material 52 crosses over the longitudinal direction side edge 34 of the absorbent article 10. In the first wing configuration, the first fold region 144 and the portion of the wing outer region 148 which are visible to the wearer in a top down view can provide the wing 50 with a first wing area.

Referring to FIGS. 3 and 4, the absorbent article 10 can have a pair of pivotable wings 50 present in a second wing configuration. In such a second wing configuration, each of the first attachment region 140 and the second attachment region 142 are bonded to the backsheet layer 44 of the absorbent article 10. The first fold line 100 is in a folded configuration such that the first fold region 144 is in an overlapping configuration with the first attachment region 141. The second fold line 110 is also folded such that a portion of the wing outer region 148 is in an overlapping configuration with the first fold region 144. Thus, in the second wing configuration, the first fold region 144 and the portion of the wing outer region 148 which is in an overlapping configuration with the first fold region 144 is not visible to a wearer when the wearer views the absorbent article 10 in a top down view observing the absorbent article 10 with the topsheet layer 40 facing the wearer. In the second wing configuration, the third fold line 120 and the fourth fold line 130 are each in an unfolded configuration. Thus, in the second wing configuration, the second fold region 146 as well as a portion of the wing outer region 148 is visible to the wearer of the absorbent article 10 when the wearer views the absorbent article 10 in a top down view observing the absorbent article 10 with the topsheet layer 40 facing the wearer.

In the second wing configuration, the wing 50 that is visible to the wearer of the absorbent article 10 when observing the absorbent article 10 in a top down view with the topsheet layer 40 facing the wearer can have a second wing length. The second wing length can be defined as the distance between the first crossover point 160 and the second crossover point 162. Each of the first crossover points, 160 and 162, are those locations where the exterior material edge 80 of the wing material 52 crosses over the longitudinal direction side edge 34 of the absorbent article 10. In various embodiments, the second wing length is greater than the first wing length. In various embodiments, the second wing length is greater than the first wing length by an increase in length of from about 5, 10, 15, 20, or 25% to about 30, 35, 40, 45, 50, 55 or 60%. In the second wing configuration, the second fold region 146 and the portion of the wing outer region 148 which are visible to the wearer in a top down view can provide the wing 50 with a second wing area. In various embodiments, the second wing area is greater than the first wing area. In various embodiments, the second wing area is greater than the first wing area by an increase in area of from about 5, 10, 15, 20, or 25% to about 30, 35, 40, 45, 50, 55, or 60%.

As described herein, when the wing material 52 is bonded to the absorbent article 10, the first fold line 100 and the fourth fold line 130 can form a straight line with an angle of 180 degrees between the two fold lines, 100 and 130. In various embodiments, the wing material 52 can be bonded to the absorbent article 10 such that the line formed by the first fold line 100 and the fourth fold line 130 can be in proximity to the longitudinal direction side edge 34 of the absorbent article 10. In various embodiments, the line formed by the first fold line 100 and the fourth fold line 130 can be parallel with the longitudinal direction side edge 34 of the absorbent article 10. During the pivoting of the wing 50 from the first wing configuration to the second wing configuration, the first fold line 100 and the fourth fold line 130, while being able to fold and unfold, remain in a fixed position with regard to the longitudinal centerline 12 of the absorbent article 10. As such, in the pivoting between the first wing configuration and the second wing configuration, neither the first fold line 100 nor the fourth fold line 130 move either toward or away from the longitudinal centerline 12 of the absorbent article 10.

As described herein, when the wing material 52 is bonded to the absorbent article 10, the second fold line 110 and the third fold line 120 can form a straight line with an angle of 180 degrees between the two fold lines, 110 and 120. During the pivoting of the wing 50 from the first wing configuration to the second wing configuration, the second fold line 120 and the third fold line 120, while being able to fold and unfold, also rotate about the wing pivot point 54. As such, the second fold line 110 moves closer to the longitudinal centerline 12 when pivoting from the first wing configuration to the second wing configuration and the third fold line 120 moves further away from the longitudinal centerline 12 when pivoting from the first wing configuration to the second wing configuration.

While FIGS. 1-4 illustrate the wings 50 of the current disclosure being bonded to an absorbent article 10 wherein the absorbent article 10 has a generally triangular shape in that the anterior region 20 is narrower in width than the central region 24 which is narrower in width than the posterior region 22, the wings 50 of the current disclosure can be bonded to an absorbent article 10 having any shape desired. In various embodiments, the absorbent article 10 can have any shape deemed suitable such as, but not limited to, oval, racetrack, hourglass, rectangular, etc.

Referring to FIGS. 1-4, the wing material 52 is illustrated as being bonded to the absorbent article 10 such that the wing pivot point 54 is positioned between the transverse centerline 14 and the first transverse direction end edge 30 of the absorbent article 10. In various embodiments, the wing material 52 can be bonded to the absorbent article 10 such that the wing pivot point 54 is positioned at the transverse centerline 14 of the absorbent article 10. In various embodiments, the wing material 52 can be bonded to the absorbent article 10 such that the wing pivot point 54 is positioned between the transverse centerline 14 and the second transverse direction end edge 32 of the absorbent article 10.

Figure 5:
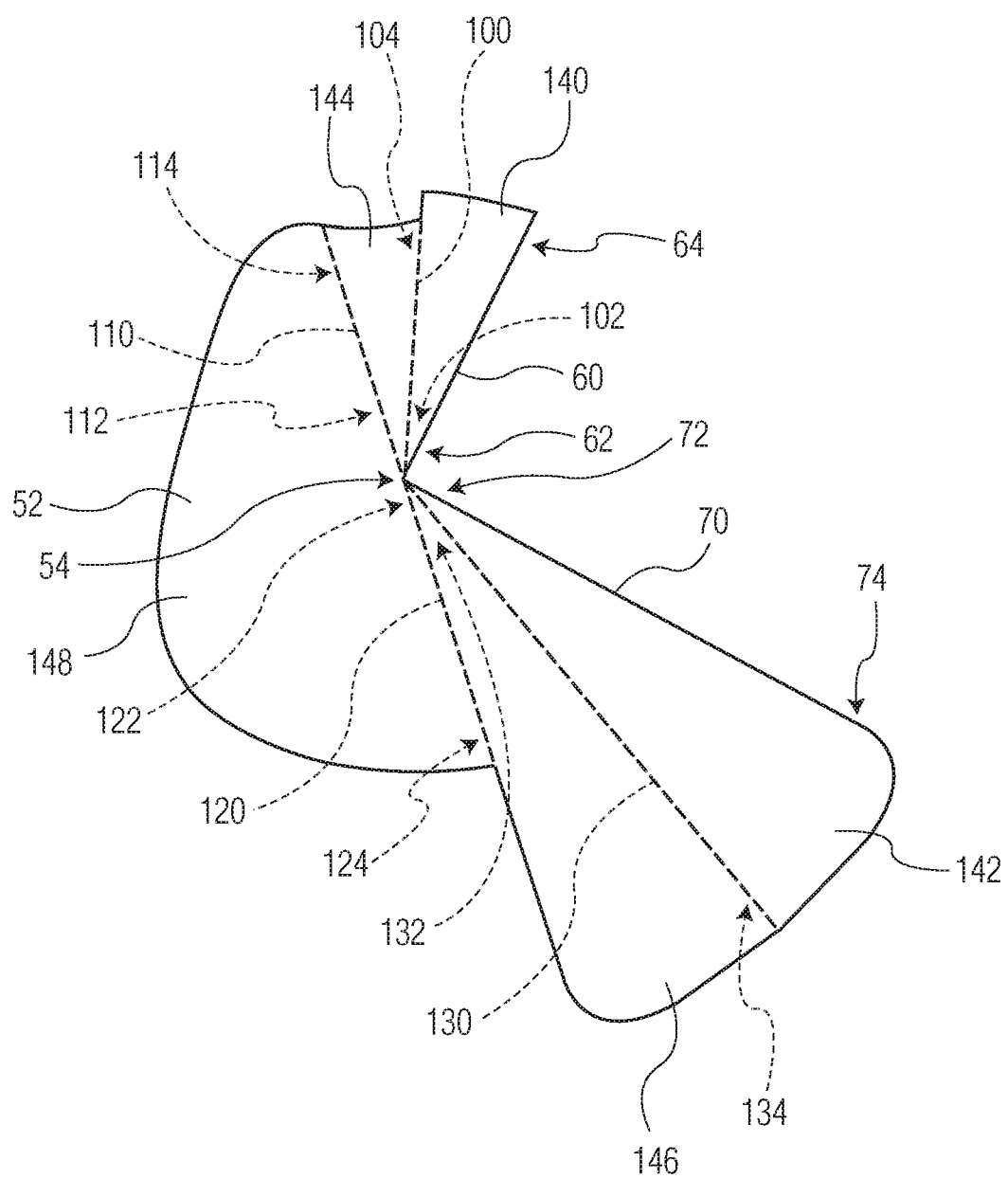
FIG. 5 is a top view of an embodiment of a wing material.
Figure 6:
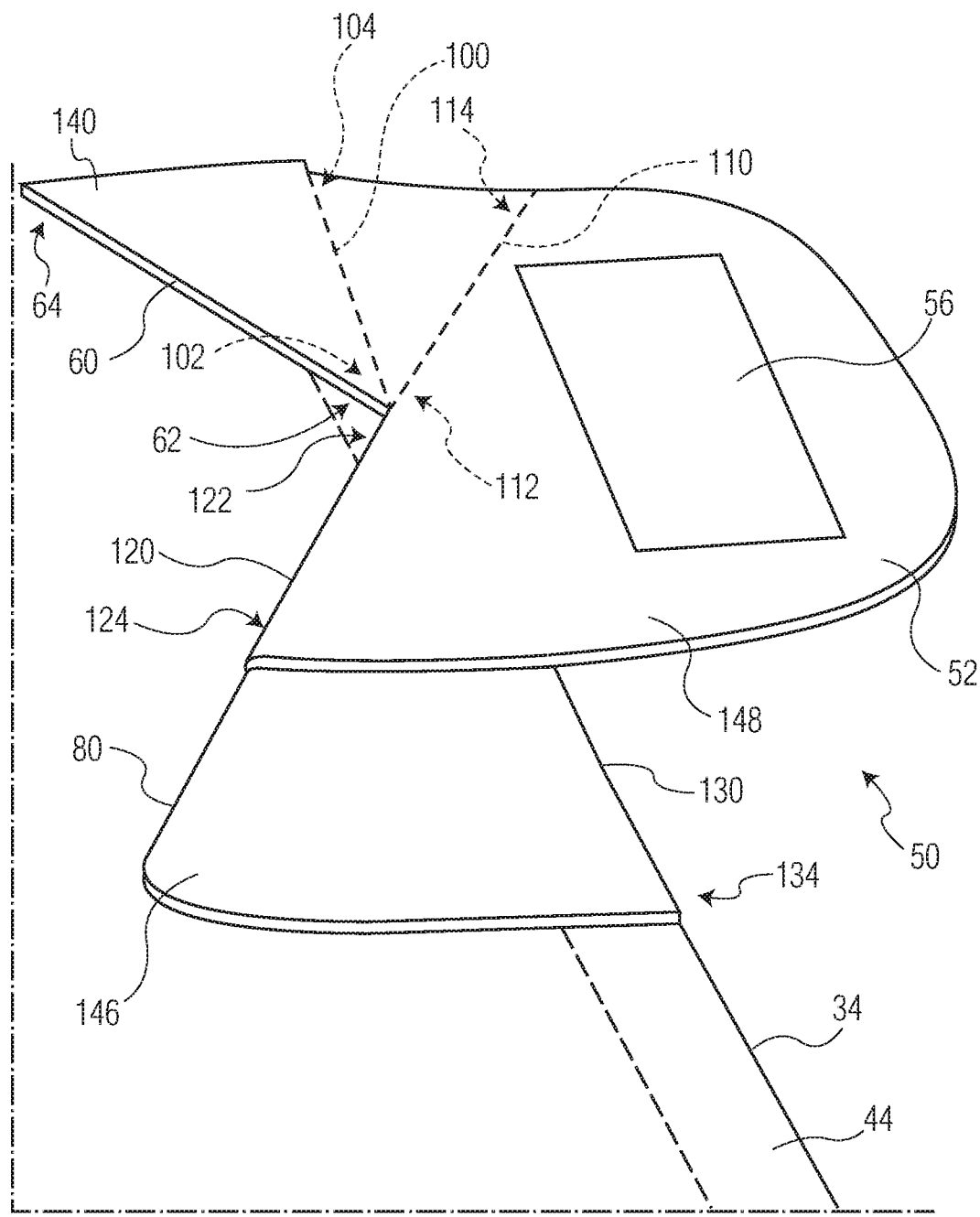
FIG. 6 is a perspective view of a close-up of a wing of an absorbent article in a first wing configuration.
Figure 7:
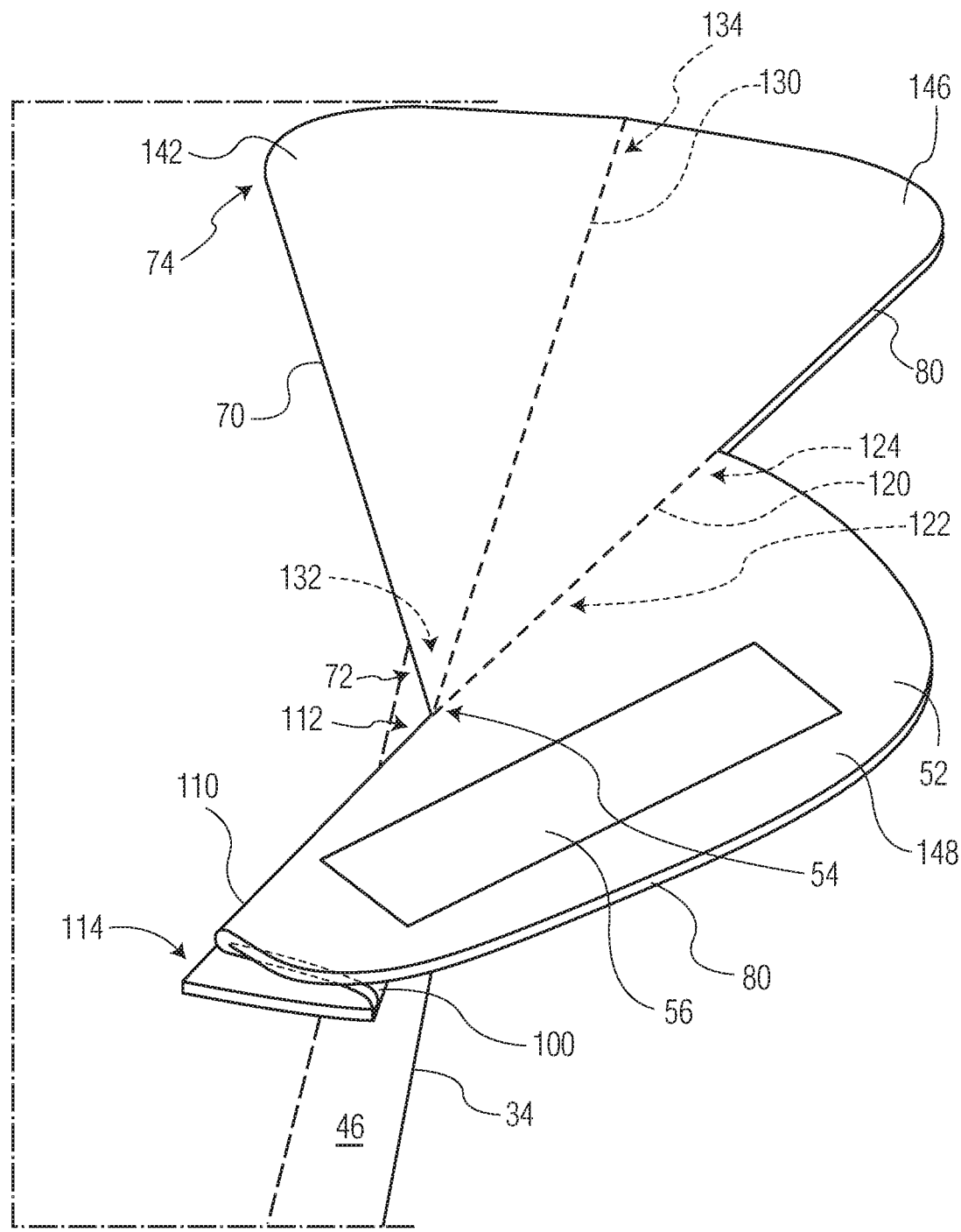
FIG. 7 is a perspective view of a close-up of a wing of an absorbent article in a second wing configuration.

FIG. 5 provides an exemplary illustration of an embodiment of a wing material 52 in an unbonded configuration (i.e., not bonded to an absorbent article 10). As illustrated in FIG. 5, the second fold line 110 and the third fold line 120 form a straight line and are at an angle of 180 degrees from each other. The first fold line 100 and the fourth fold line 130, however, are not forming a straight line with each other, i.e., they are not at a 180 degree angle with each other, such as is desired when bonded to the absorbent article 10. As illustrated in FIG. 5, the material interior edges, 60 and 70, are at an angle of 90 degrees to each other. As described herein, the angle between the material interior edges, 60 and 70, when the wing material 52 is not bonded to an absorbent article 10 can be from about 0, 15, 30, 45 or 70 degrees to about 90, 115, 145, 160, or 180 degrees. To put the first fold line 100 into a 180 degree angle with the fourth fold line 130, the material interior edges, 60 and 70, are moved further apart from each other thereby increasing the angle between the material interior edges, 60 and 70. Doing this will align the first fold line 100 with the fourth fold line 130 and will create a ripple in the wing material 52. The wing material 52 is then bonded to the absorbent article 10 with the pairings of fold lines in alignment with each other (i.e., the first fold line 100 is aligned with the fourth fold line 130 and the second fold line 110 is aligned with the third fold line 120). The wing material 52 can then be placed into either the first wing configuration or the second wing configuration which will eliminate the rippled in the wing material 52. To place the wing material into the first wing configuration the third fold line 120 and the fourth fold line 130 can be folded. FIG. 6 provides an illustration of an embodiment of a perspective view of a close-up of a wing 50 in the first wing configuration. To place the wing material 52 into the second wing configuration the first fold line 100 and the second fold line 110 can be folded. FIG. 7 provides an illustration of an embodiment of a perspective view of a close-up of a wing 50 in the second wing configuration.

Garment Attachment:

The absorbent article 10 can be provided with a garment attachment 170 which can be located on the garment facing surface 46 of the backsheet layer 44 for attachment of the absorbent article 10 to a wearer's undergarment. The garment attachment 170 can be provided in any suitable arrangement and/or pattern on the garment facing surface 46 of the backsheet layer 44 as deemed suitable. The garment attachment 170 can include any suitable attachment mechanism, such as, but not limited to, adhesive, cohesive, hooks, snaps, clips, or the like, or combinations thereof.

Figure 8:
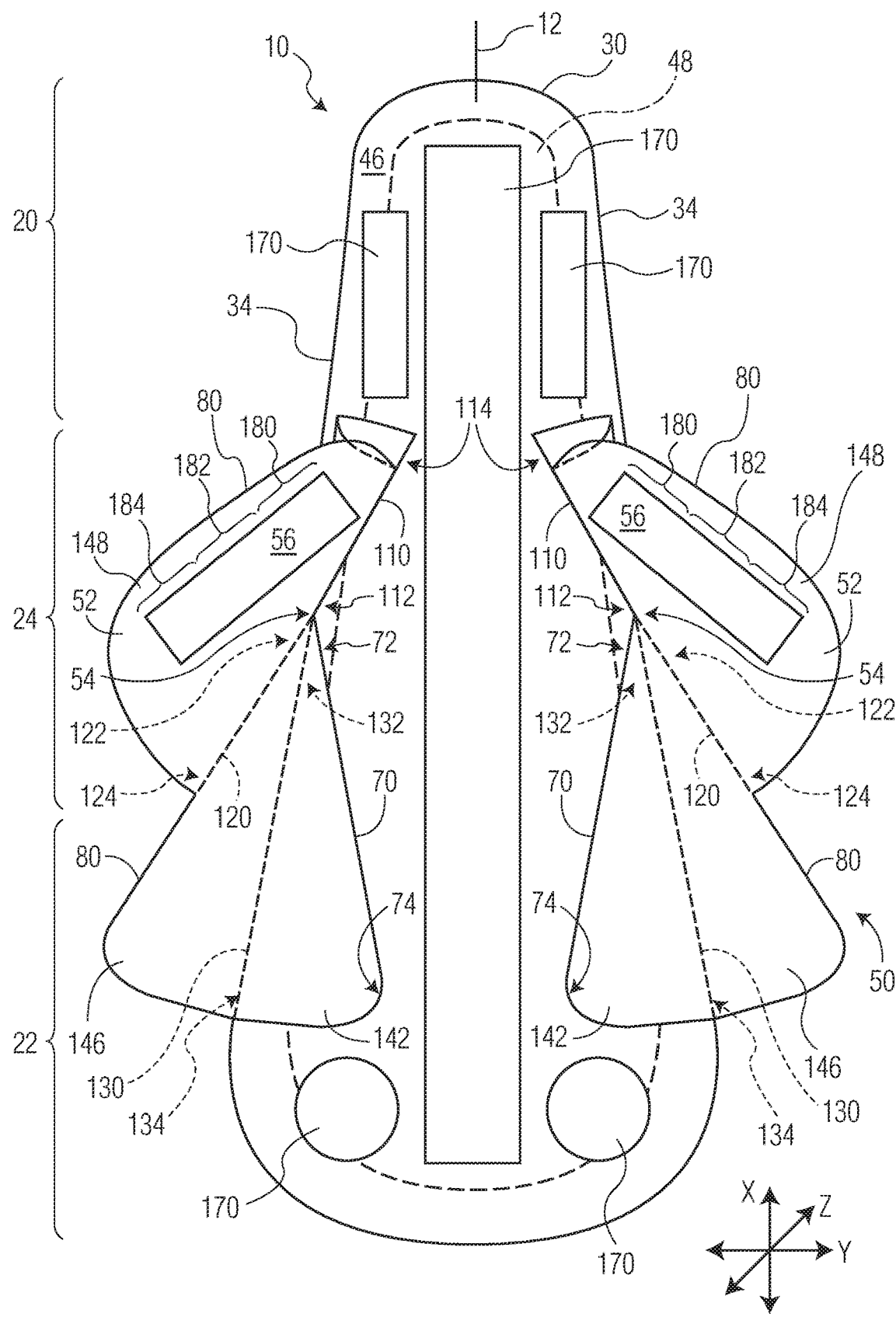
FIG. 8 is a bottom view of an embodiment of an absorbent article with the wings in a second wing configuration.

In various embodiments, the garment attachment 170 can be provided in any amount suitable on the garment facing surface 46 of the backsheet layer 44. In various embodiments, the garment attachment 170 can be provided in any pattern as deemed suitable, such as, but not limited to, stripes, swirls, dots, or the like, or combinations thereof. The garment attachment 170 can be provided in any location on the garment facing surface 46 of the backsheet layer 44 as deemed suitable. While the garment attachment 170 can be provided in any amount, any pattern, and in any location on the garment facing surface 46 of the backsheet layer 44, the garment attachment 170 does not interfere with the functionality of the pivotable wings 50 of the absorbent article 10. For example, the garment attachment 170 is not placed in an overlapping configuration with the pivotable wings 50 as this may cause interference with the functionality of the wings 50 and may prevent the wings 50 from rotating about the wing pivot point 54 as desired by the wearer of the absorbent article 10. FIGS. 2 and 4 provide an exemplary illustration of a garment attachment 170 which is present as a single continuous stripe in the longitudinal direction (X) of the absorbent article 10. It should be understood that the garment attachment 170 can be present in any pattern as deemed suitable to maintain the absorbent article 10 in the proper positioning within the wearer's undergarment. Additional garment attachment 170 could be present, in addition to the single stripe that is illustrated in FIGS. 2 and 4, such as, for example, smaller stripes or dots of garment attachment 170 can be positioned in the anterior region 20 and/or the posterior region 22 of the garment facing surface 46 of the backsheet layer 44 in locations which would not interfere with the functionality of the wings 50. FIG. 8 provides an exemplary illustration of additional garment attachment 170—smaller rectangular strips in the anterior region 20 and dots in the posterior region 170 of the absorbent article 10. FIG. 8 also provides an exemplary illustration of the narrowing, in the transverse direction (Y) of the central longitudinal stripe of garment attachment 170 that extends in the longitudinal direction (X). Such narrowing can be the result of the positioning of the wing pivot points 54 of the wings 50 at a distance, in the transverse direction (Y) away from the longitudinal direction side edges 34.

Figure 9:
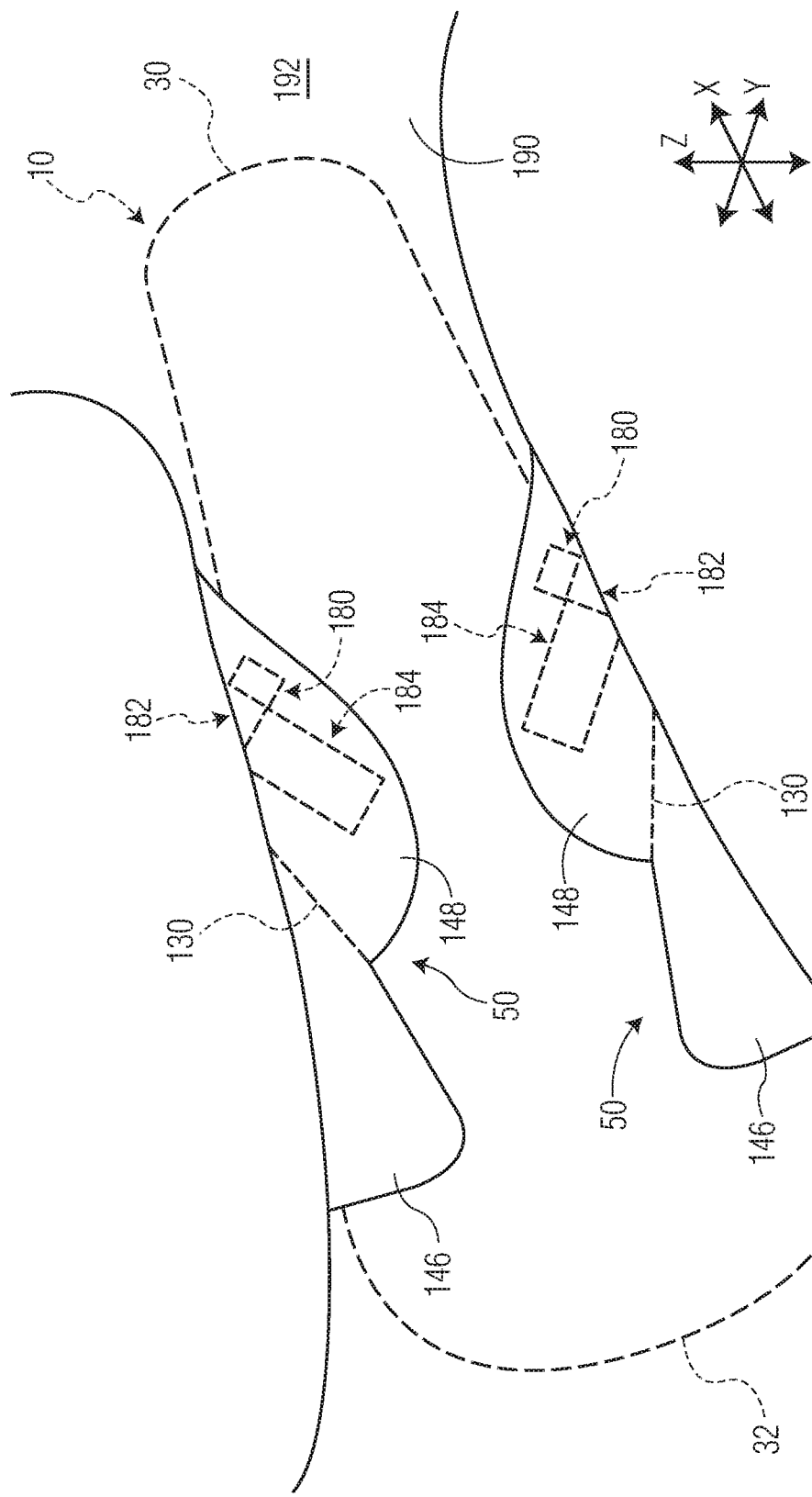
FIG. 9 is a perspective bottom view of the absorbent article of FIG. 8 in which the wings are folded over and onto the garment facing surface of a wearer's underwear.

Multi-Surface Contact Attachment Aid:

In various embodiments, the attachment aid 56 of the pivotable wings 50 can be positioned on the wings 50 such that when the wearer wraps the wings 50 around their undergarment, the attachment aid 56 can make contact with multiple surfaces of the wearer's undergarment. Referring to FIGS. 8 and 9, the attachment aid 56 can be divided into three segments: a first segment 180, a second segment 182, and a third segment 184. In various embodiments, each of the three segments, 180, 182, and 184, can be equal in length. In various embodiments, two of the three segments 180, 182, or 184, can be equal in length and one of the three segments, 180, 182, or 184, can have a length different from the other two segments. In various embodiments, each of the three segments, 180, 182, and 184, can have a length different from the other segments, 180, 182, and 184. The first segment 180 can be the portion of the attachment aid 56 which can maintain contact with the wearer facing surface of the wearer's undergarment 190 when the absorbent article 10 is in use by the wearer. The second segment 182 can be the portion of the attachment aid 56 which can maintain contact with each of the side seams of the wearer's undergarment 190—the wearer facing surface of the side seam, the thigh facing surface of the side seam, and the garment facing surface of the side seam when the absorbent article 10 is in use by the wearer. The third segment 184 can be the portion of the attachment aid 56 which can maintain contact with the garment facing surface 192 of the wearer's undergarment 190 when the absorbent article 10 is in use by the wearer.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a first transverse direction end edge, a second transverse direction end edge, and a pair of longitudinal direction side edges extending between and connecting the first transverse direction end edge and the second transverse direction end edge;
   b. a topsheet layer, a backsheet layer, and an absorbent core positioned between the topsheet layer and the backsheet layer;
   c. a longitudinal direction centerline;
   d. a pair of wings bonded to the backsheet layer, each of the pair of wings comprising a wing material, each wing material comprising:
      i. a wing pivot point;
      ii. a first material internal edge which has a first proximal end and a first distal end and a second material internal edge which has a second proximal end and a second distal end, wherein the first proximal end and the second proximal end of the respective first material internal edge and the second material internal edge join together at the wing pivot point and each of the first material internal edge and the second material internal edge extend in a direction away from the wing pivot point and towards the longitudinal direction centerline;
      iii. an exterior material edge extending between and connecting the first distal end and the second distal end of the respective first material internal edge and the second material internal edge and extending in a direction away from the longitudinal direction centerline such that at least a portion of the exterior material edge extends beyond one of the longitudinal direction side edges of the absorbent article;

iv. a first fold line having a third proximal end and a third distal end, a second fold line having a fourth proximal end and a fourth distal end, a third fold line having a fifth proximal end and a fifth distal end, and a fourth fold line having a sixth proximal end and a sixth distal end, wherein each of the third proximal end, the fourth proximal end, the fifth proximal end, and the sixth proximal end join together at the wing pivot point and each of the first fold line, second fold line, third fold line, and fourth fold line extend from the wing pivot point to the exterior material edge; and v. a first attachment region bordered by the first material internal edge, the first fold line, and a portion of the exterior material edge; a second attachment region bordered by the second material internal edge, the fourth fold line, and a portion of the exterior material edge; a first fold region bordered by the first fold line, the second fold line, and a portion of the exterior material edge; a second fold region bordered by the third fold line, the fourth fold line, and a portion of the exterior material edge, and a wing outer region bordered by the second fold line, the third fold line, and a portion of the exterior material edge.

2. The absorbent article of claim 1 wherein each of the first fold line and second fold lines are in an unfolded configuration such that at least a portion of the wing outer region and a portion of the first fold region extend beyond the longitudinal direction side edges of the absorbent article, and each of the third fold lines and fourth fold lines are in a folded configuration such that at least a portion of the wing outer region and the second fold region is positioned in an overlapping configuration with the backsheet layer.

3. The absorbent article of claim 1 wherein each of the first fold line and second fold lines are in a folded configuration such that the first fold region is positioned in an overlapping configuration with the backsheet layer, and each of the third fold lines and the fourth fold lines are in an unfolded configuration such that at least a portion of the wing outer region and the second fold region extend beyond the longitudinal direction side edges of the absorbent article.

4. The absorbent article of claim 1 wherein the first fold line and the fourth fold line are at a 180 degree angle to each other.

5. The absorbent article of claim 1 wherein the second fold line and the third fold line are at a 180 degree angle to each other.

6. The absorbent article of claim 1 wherein the first fold line and the fourth fold line are parallel to the longitudinal direction side edge.

7. The absorbent article of claim 1 wherein the first fold line and the fourth fold line are in a fixed spatial relationship to the longitudinal direction centerline.

8. The absorbent article of claim 1 wherein the second fold line and the third fold line can rotate their spatial relationship to the longitudinal direction centerline.

9. The absorbent article of claim 1 wherein the first fold line is at an angle to the second fold line of from about 5 degrees to about 85 degrees.

10. The absorbent article of claim 1 wherein the third fold line is at an angle to the fourth fold line of from about 5 degrees to about 85 degrees.

11. The absorbent article of claim 1 wherein an angle between the first fold line and the second fold line is the same as an angle between the third fold line and the fourth fold line.

12. The absorbent article of claim 1 wherein the wing pivot point is located proximal to one of the longitudinal direction side edges.

13. The absorbent article of claim 1 wherein the wing pivot point is located at a distance, in a transverse direction of the absorbent article, away from one of the longitudinal direction side edges.

14. The absorbent article of claim 1 further comprising a garment attachment.

15. The absorbent article of claim 14 wherein the garment attachment does not interfere with the functionality of the wings.

* * * * *